United States Patent
Polczynski et al.

(10) Patent No.: US 6,380,746 B1
(45) Date of Patent: Apr. 30, 2002

(54) MONITORING FLUID CONDITION WITH A SPIRAL ELECTRODE CONFIGURATION

(75) Inventors: Mark H. Polczynski, Elm Grove; Paul G. Rops, Germantown; Robert A. Bauer, Milwaukee; Martin A. Seitz, Brookfield; Richard W. Hirthe, Milwaukee, all of WI (US)

(73) Assignee: Eaton Corporation, Cleveland, OH (US)

( * ) Notice: Subject to any disclaimer, the term of this patent is extended or adjusted under 35 U.S.C. 154(b) by 0 days.

(21) Appl. No.: 09/432,971

(22) Filed: Nov. 3, 1999

(51) Int. Cl.$^7$ .............................................. G01N 27/07
(52) U.S. Cl. ..................... 324/446; 324/439; 324/441; 324/450; 324/698; 324/724
(58) Field of Search ................................. 324/439, 441, 324/444, 446, 450, 639, 693, 698, 707, 722, 724

(56) References Cited

U.S. PATENT DOCUMENTS

| | | | | |
|---|---|---|---|---|
| 4,449,396 A | * | 5/1984 | Bzdula .................... 324/696 X |
| 4,646,070 A | | 2/1987 | Yasuhara et al. ........... 340/603 |
| 4,733,556 A | | 3/1988 | Meitzler et al. ............... 73/64 |
| 4,757,252 A | | 7/1988 | Maltby et al. ............... 324/687 |
| 4,922,180 A | * | 5/1990 | Saffer et al. ................ 324/639 |
| 5,008,628 A | * | 4/1991 | Krigmont et al. ........... 324/693 |
| 5,151,660 A | | 9/1992 | Powers et al. .............. 324/689 |
| 5,208,544 A | | 5/1993 | McBrearty et al. ......... 324/687 |
| 5,274,335 A | | 12/1993 | Wang et al. ................. 324/689 |
| 5,382,942 A | | 1/1995 | Raffa et al. ................. 340/457.4 |
| 5,388,448 A | * | 2/1995 | Showalter et al. ....... 324/693 X |
| 5,389,883 A | | 2/1995 | Harper ....................... 324/636 |
| 5,543,722 A | | 8/1996 | Suzuki et al. ............... 324/675 |
| 5,889,200 A | | 3/1999 | Centers et al. ............. 73/53.01 |

OTHER PUBLICATIONS

"The Applications of AC Impedance Technique For Detecting Glycol Contamination in Engine Oil" by S. S. Wang, et al., published Jan. 4, 1997 by Elselvier Science S.A.
"The Applications of AC Impedance Technique For Detecting Glycol Contamination in Engine Oil" by S. S. Wang, et al., published Jan. 4, 1997 by Elselvier Science S.A.
"Novel Sensors for Portable Oil Analyzers", 1998 (no month).

(List continued on next page.)

Primary Examiner—Glenn W. Brown
Assistant Examiner—Wasseem H. Hamdan
(74) Attorney, Agent, or Firm—Roger A. Johnston

(57) ABSTRACT

A plug for insertion through the wall of a vessel filled with fluid to be monitored has an extension immersed in the fluid which has a pair of wire electrodes helically wound thereon in spaced arrangement. The electrodes are wound at a uniform pitch in one embodiment and wound with regions of closely and widely spaced pitches in another embodiment. In a third embodiment, the electrodes are helically wound in spaced parallel arrangement at a pitch greater than the spacing of the pair. A thermistor is disposed on the extension for providing a fluid temperature signal. The electrodes are excited sequentially by a low voltage at a fractional Hertz (low) frequency and a (high) frequency of at least one Hertz and the current and temperature are measured. The impedance and differential impedance are computed from the measured currents. From stored values of the differential impedance as a function of temperature for various known fluid conditions, the condition of the fluid is determined; and, if greater than a predetermined threshold, an alarm is activated and/or the fluid condition displayed.

19 Claims, 7 Drawing Sheets

OTHER PUBLICATIONS

Case Western Reserve University, Cleveland, Ohio Dept. of Physics NTIS 19980624 080.

"AC Impedance Measurements of the Resistance and Capacitance of Lubricants" by S. S. Wang, et al, published Jun. 13, 1986 ASLE Transactions vol. 30,4,436–443.

The Development of in situ Electrochemical Oil–Condition Sensors by S. S. Wang, et al., Published by Elsevier Sequoia, 1994 (no month).

"Development of an Automatic Engine Oil–Change Indicator System" by Shirley E. Schwartz and Donald J. Smolenski, published Feb. 1987 Society of Automotive Engineers

* cited by examiner

US 6,380,746 B1

MONITORING FLUID CONDITION WITH A SPIRAL ELECTRODE CONFIGURATION

BACKGROUND OF THE INVENTION

The present invention relates to real time monitoring of the condition of a fluid in a vessel as, for example, oil in the sump of an internal combustion engine or a power transmission. An example of such a device is that shown and described in copending application of Robert A. Bauer, et al. "FLUID CONDITION MONITOR", Ser. No. 09/220,556, filed Dec. 23, 1998, now U.S. Pat. No. 6,278,281, and assigned to the assignee of the present invention. The aforesaid Bauer, et al. application describes monitoring fluid condition with a probe having spaced parallel electrodes preferably in the form of parallel plates and exciting the probe sequentially at a first low and a second high voltage and measuring the difference of the magnitude in current at the first and second excitations. The difference in measured current is then compared with stored values in a lookup table of values of the difference in current for known fluid conditions; and, the condition of the fluid then determined in real time. A microcomputer then outputs a signal if the measured fluid condition is at a pre-designated threshold, as for example, one not suitable for further use.

The parallel plate probe of the aforesaid Bauer, et al. application, although generally useful, has been found somewhat cumbersome and difficult to install in certain closed fluid vessels such as engine oil sumps and power transmission housings inasmuch as the probe must have sufficient electrode surface area, be robust, reliably sealed to prevent loss of fluid and able to withstand the elevated temperatures of engine and power transmission lubricant. The aforesaid parallel plate type probe has been found prohibitively large in engine and transmission lubricant monitoring applications inasmuch as the required surface area of the electrode plates has dictated the minimum size; and, this has resulted in a requirement prohibitively large opening or aperture for a probe insertion in an engine sump or transmission casing.

Accordingly, it has been desired to provide a probe assembly for fluid monitoring particularly by relatively low voltage probe excitation at fractional Hertz frequencies and which is sufficiently small and rugged for insertion in a minimally sized opening in the fluid vessel and particularly an engine sump or transmission casing.

BRIEF SUMMARY OF THE INVENTION

The present invention provides a probe for relatively low voltage, low current monitoring of fluid condition in which fractional Hertz probe excitation is utilized for measuring probe current.

The probe assembly of the present invention has a configuration which enables the probe to be inserted through an aperture or opening having a minimal size and thus is particularly suitable for installation in an engine oil sump or power transmission casing. The probe of the present invention employs a pair of electrodes in wire form which are spirally wound on a support or core for immersion through the aperture in the vessel and into the fluid to be monitored. The ends of the electrodes are attached to leads which extend through the support structure, preferably in the form of a threaded plug, which is inserted in the fluid vessel opening and sealed therein. In one embodiment, the spiral wires are wound in spaced helical configuration. In a variation, the spiral winding has a region of a first uniform pitch another region is wound at a second uniform pitch of about twice the first pitch spacing. In another embodiment, the pair of wire electrodes are wound together in uniformly spaced parallel arrangement at a desired uniform pitch.

The probe assembly of the present invention thus lends itself to insertion in the wall of the fluid vessel through a minimally sized opening; and, fabrication and installation of the probe are greatly simplified.

DETAILED DESCRIPTION OF THE INVENTION

The present invention relates to the subject matter of co-pending application of Robert A. Bauer, et al. "Fluid Condition Monitor", Ser. No. 09/220,556, filed Dec. 23, 1998, now U.S. Pat. No. 6,278,281, assigned to the assignee of the present invention and incorporated herein by reference.

Figure 2:
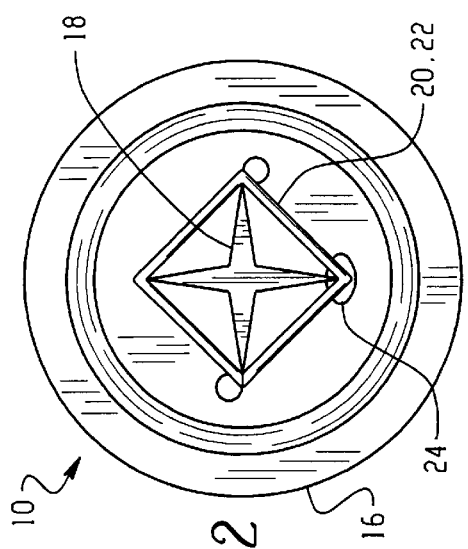
FIG. 2 is a top view of the embodiment of FIG. 1.
Figure 1:
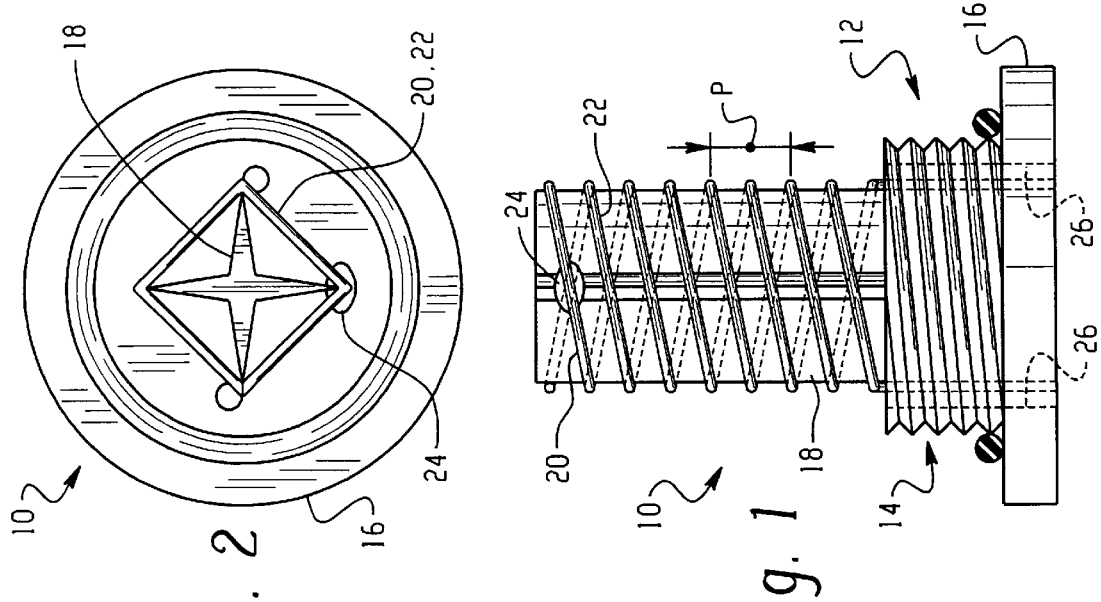
FIG. 1 is a side elevation view of one embodiment of the invention.
Figure 6:
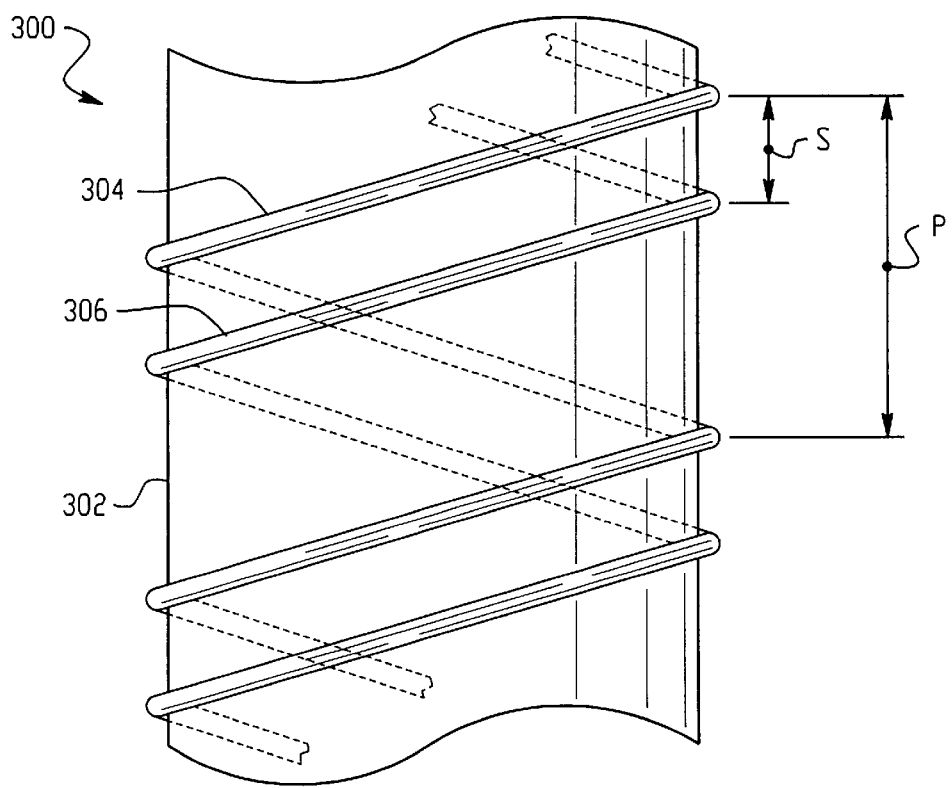
FIG. 6 is a view similar to FIG. 4 of a further embodiment of the invention.

Referring to FIGS. 1, 2 and 6, the probe assembly of the present invention is indicated generally at 10 and includes a plug or base indicated generally at 12 and having a threaded shank portion 14. The plug 12 also preferably has an enlarged diameter radially outwardly extending flange portion 16 to facilitate installation and may have flats or a hexagonal shape; and, the plug is also provided with a generally elongated support portion 18 extending axially from the threaded portion 14. Referring to FIG. 2, the support portion 18 has a ribbed or cruciform configuration in transverse section in the embodiment of FIG. 1, but may have other configurations such as, for example, tubular which will be hereinafter described.

Figure 4:
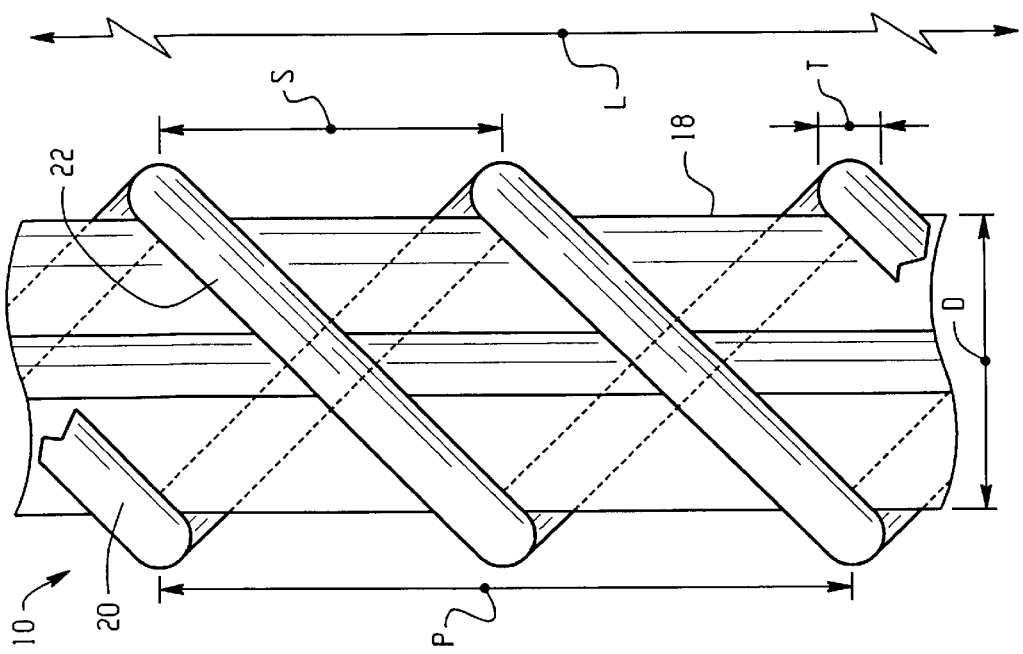
FIG. 4 is an enlarged view of a portion of the embodiment of FIG. 1.

Referring to FIG. 4, support 18 has spirally wound thereon a pair of wire electrodes denoted respectively 20, 22 disposed in spaced spiral, preferably helical, arrangement having a pitch denoted by the reference character P with the electrodes axially interdigitated in generally equally spaced arrangement by the spacing denoted by the reference character S, which is equal to half of the pitch P. The transverse dimension of the support 18 is denoted in FIG. 4 by the reference character D. The thickness or wire diameter of the electrodes 20, 22 is denoted in FIG. 4 by the reference character T. In the presently preferred practice of the invention, the support is made of material having a high electrical resistance and low dielectric constant to minimize leakage in view of the low voltage excitation of the probe employed in the electro-impedance techniques such as described as in the aforementioned application of Bauer, et al. In the present practice of the invention, the probe assembly of the present invention is intended to monitor the condition of synthetic motor oil such as that designated 5W–30 and commonly used in passenger car engines or transmission fluid employed in heavy or light duty truck transmissions or passenger car automatic transmissions. For a passenger car motor oil (PCMO) application a satisfactory probe has been used having the dimensions set forth in Table I below.

TABLE I

L = 1.5" (38 mm)
D = .289" (7.3 mm)
S = .010–.050" (.25–1.27 mm)
P = 2 S
T = .018 (.46 mm)

In the present practice of the invention a probe having the dimensions set forth in Table I has also been employed for mineral based PCMO with satisfactory results. It will be understood however that modifications to the above dimensions may be made to accommodate the desired support transverse dimension. If a smaller dimension D is employed, the length of the helical winding for the wires 20, 22 will necessarily be increased to provide the same amount of electrode surface for providing the desired electrical sensitivity.

If desired, a temperature sensing thermistor 24 is mounted on support 18; and, separate leads are connected thereto and extend through holes 26 provided in the plug 12 as indicated by dashed line in FIG. 1.

Figure 3:
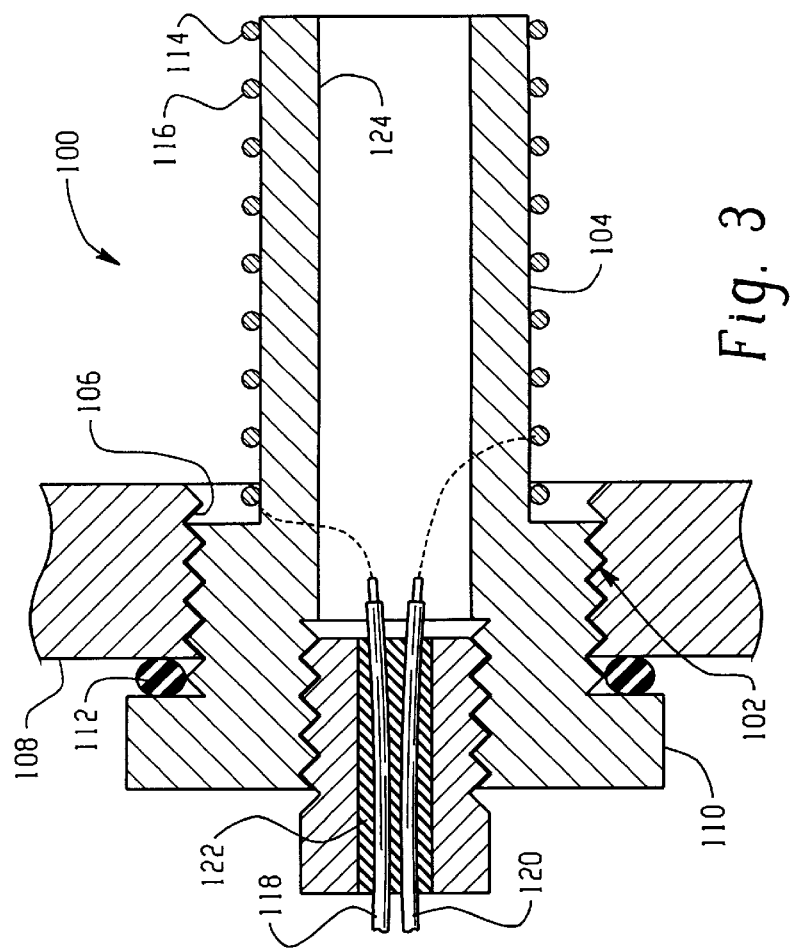
FIG. 3 is a cross-section of another embodiment of the present invention as installed in a fluid vessel.

Referring to FIG. 3, another embodiment of the invention is indicated generally at 100 and employs a threaded plug denoted generally at 102 which has an elongated support 104 extending therefrom which has a hollow tubular configuration as shown in FIG. 3. The plug is illustrated as received in a threaded bore 106 provided in the wall of the fluid vessel denoted by reference numeral 108. Plug 102 has an enlarged diameter flange 110 which seals against the outer surface of the casing 108 by a suitable O-ring 112. A pair of wire electrodes 114, 116 helically wound on support 104 are shown in cross-section. It will be understood that the support 104 may have a polygonal or circular configuration on its outer periphery in transverse section (not shown) taken at right angles to the axis of the helically wires wound 114, 116.

A pair of electrical leads 118, 120 are disposed in a suitable fitting threaded into the flanged end of the plug 102; and, the leads are sealed therein by suitable potting material 122. One end of each of the leads 118, 120 extends into the bore 124 of the support 104 and the leads are each respectively attached to one of the electrode wires 114, 116 as indicated by dashed lines in FIG. 3.

Figure 5:
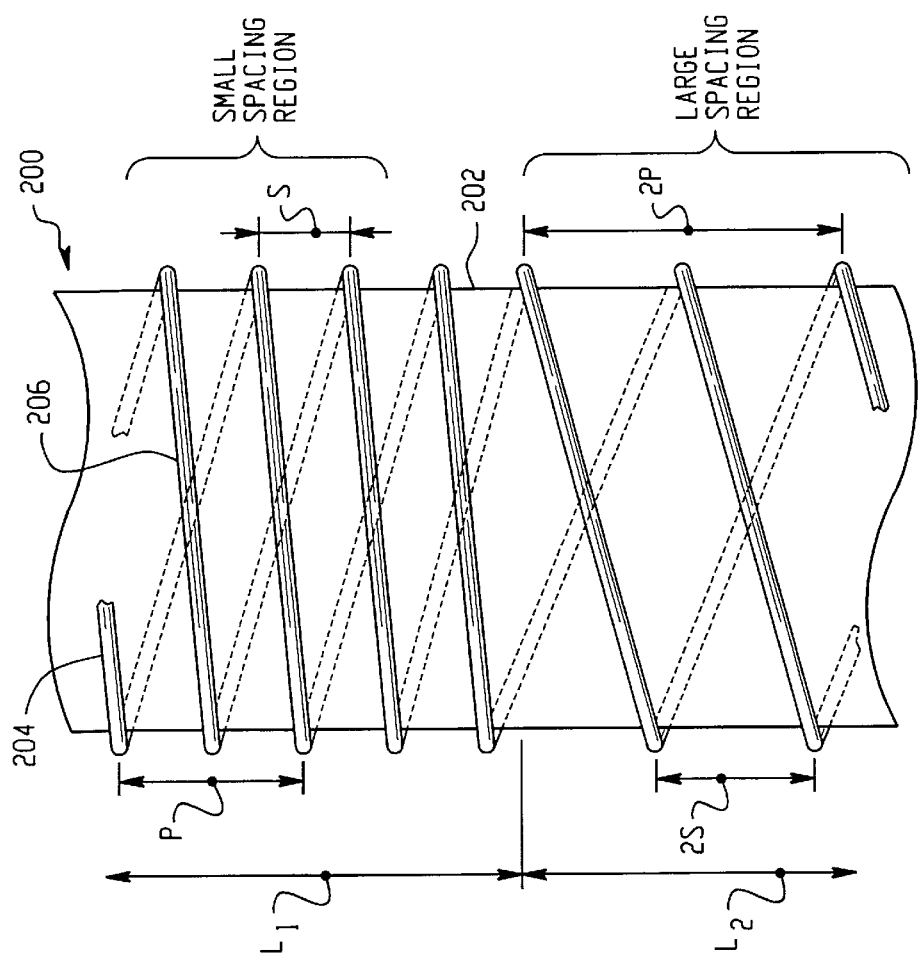
FIG. 5 is a view similar to FIG. 4 of another embodiment of the invention.
Figure 7:
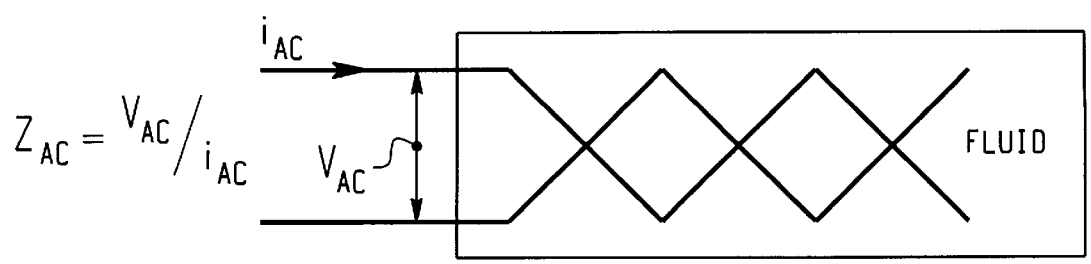
FIG. 7 is an electrical equivalent diagram of the embodiment of FIG. 1.

Referring to FIG. 5, another embodiment of the probe is indicated generally at 200 and has a support or rod 202 about which are wrapped or wound in helically spaced arrangement, two electrode wires 204, 206 and which are wound for a distance $L_1$ at a pitch P and spacing S where S is preferably one-half P. The wires are continued in a spiral arrangement for the length $L_2$ at an increased pitch which in the presently preferred practice is about 2P and have a spacing of 2S. The dual pitch spiral arrangement of the embodiment 200 utilizes the region of pitch P and spacing S for the length L1 and labeled "Small spacing region" in FIG. 4 as a region having increased sensitivity to surface impedance at the interface of the fluid and the electrode; whereas the region having spacing 2S and pitch 2P for the length $L_2$ and labeled "Large spacing region" in FIG. 4 has an increased sensitivity to the bulk impedance of the fluid. Thus, the arrangement of FIG. 4 provides a way of increasing the sensitivity of the probe to both electrochemical phenomena measured by the current in the probe. It will be understood with reference to FIG. 7 that the current is proportional to the change in impedance for a constant voltage excitation; and, therefore, is the electrical analog of the change in the total impedance $Z_{AC}$. It will be understood that $Z_{AC}$ is the sum of the impedance due to the change in the resistance and the capacitive reactance detected by the probe which are effected by the changes in the bulk impedance of the current flow through the fluid and the impedance due to surface effects of the electrode.

Referring to FIG. 6, another embodiment indicated generally at 300 has a support or rod 302 which is attached to a plug portion (not shown) but which is similar to the plug 12 of FIG. 1. The rod 302 has wrapped therearound a pair of electrode wires 304, 306 which are disposed in spaced preferably parallel helical arrangement with a parallel spacing denoted by S and a pitch denoted by P. The embodiment 300 a different pitch in that the pitch P is greater than 2S or twice the spacing. It will be understood that increasing the pitch will increase the length of the probe to provide the same amount of electrodes.

In the presently preferred practice of the invention the support 18, 104, 202, 302 is preferably formed of a material having a low dielectric constant (high dielectric properties), a high bulk resistance and a high surface resistance preferably not less then $10^{12}$ Ohms-cm. In the presently preferred practice the rod portions are formed of polytetrafluoroethylene (PTFE) material, but it will be understood that other materials may be used as, for example, polyphenylenesulfide or any other material stable in lubricating oil temperatures up to about 150 C. In the presently preferred practice of the invention, the electrode wires are formed of AISI type 303 stainless steel, but other suitable materials may be used.

Figure 8:
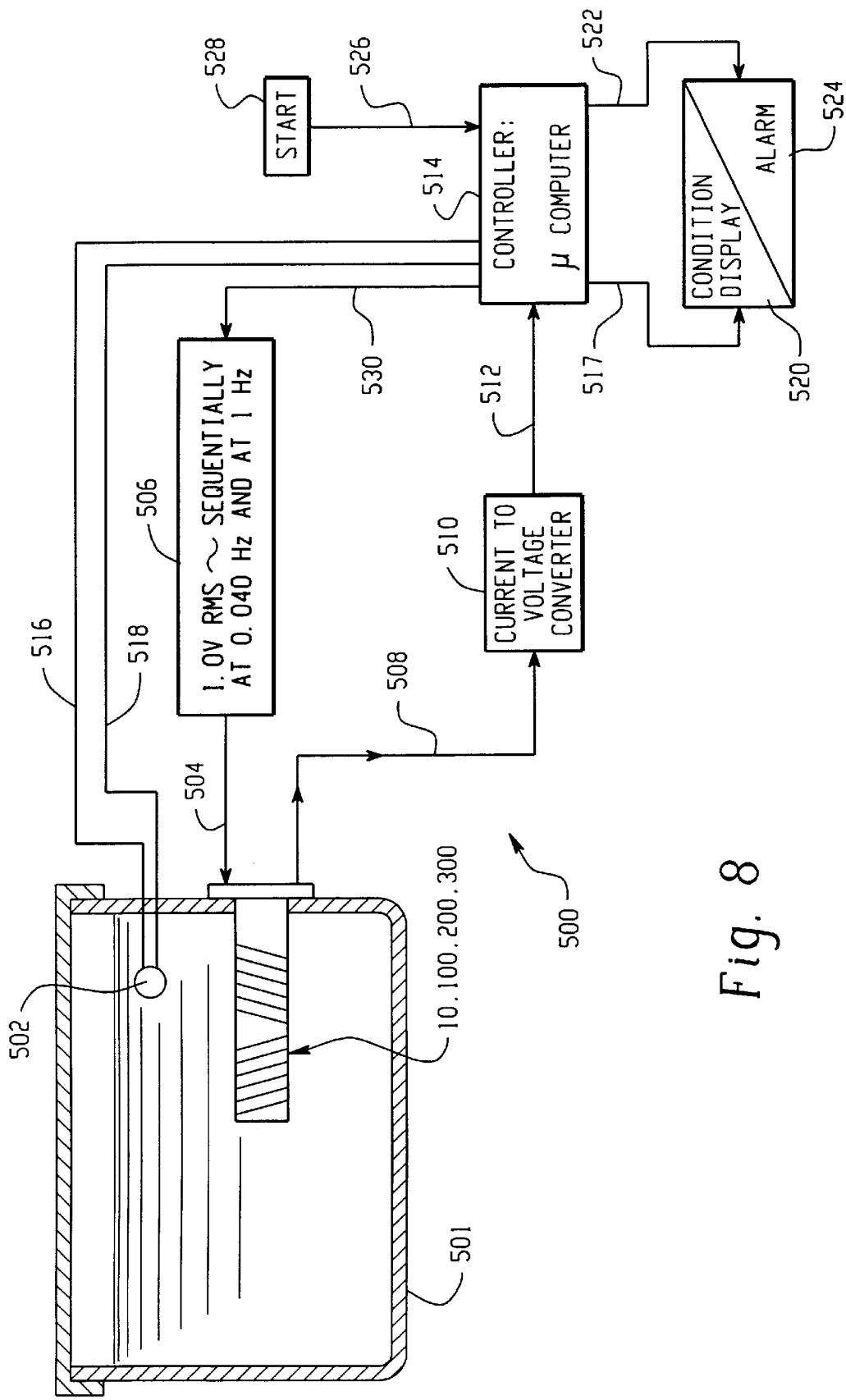
FIG. 8 is a block diagram of a system employing the present invention with fractional Hertzian (low) frequency and Hertzian (high) frequency low voltage probe excitation.

Referring to FIG. 8, the system 500 is shown employing the present invention wherein the probe assembly 10, 100, 200, 300 of the present invention is immersed in fluid contained in a vessel 501 having a temperature sensing thermistor 502 disposed therein. The probe assembly 10, 100, 200, 300 receives constant voltage excitation at 1.0 volts RMS along lead 504 sequentially at 0.04 Hertz and then at 1 Hertz from a source of excitation 506. The probe 10, 100, 200, 300 is connected through its other lead 508 to the input of a current to voltage converter 510 which provides an output along line 512 to the input of a controller 514 including a microcomputer. The microcomputer within controller 514 is connected to a temperature sensor such as thermistor 502 by leads 516, 518 and measures the temperature of fluid in vessel 501 by detecting changes in the resistance of thermistor 502 in a manner well known in the art. Although thermistor 502 is shown schematically separately mounted in FIG. 8, it will be understood that the thermistor may be mounted on the probe 10, 100, 200, 300 in the manner shown in FIG. 1. Controller 514 has an output connected along line 517 to activate a condition display 520 and/or provides an output along line 522 connected to an operator alarm 524.

The controller 514 receives an input along line 526 from a user initiated start 528, for example, an engine ignition system switch; and, controller 514 outputs a signal along line 530 to activate the voltage source 506.

Figure 9:
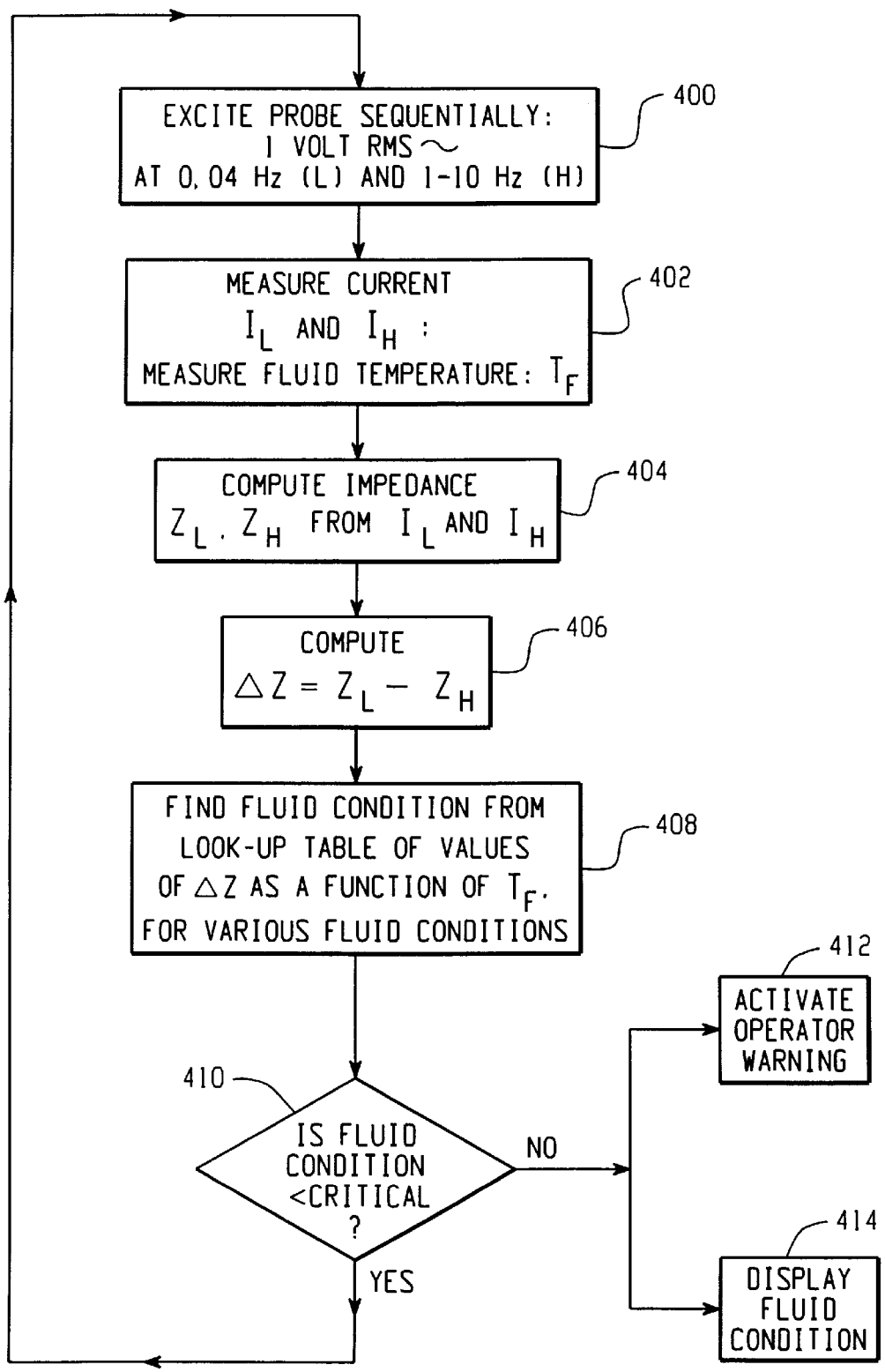
FIG. 9 is a flow diagram of the program for the controller of the system of FIG. 8.

Referring to FIG. 9, a flow diagram is shown for the operation of the controller 514 of FIG. 8 wherein the probe 10, 100, 200, 300 is excited at step 400 at about one volt RMS sequentially at a relatively low frequency (L) 0.04 Hertz and at a relatively high frequency (H) of 1–10 Hertz. The system proceeds to step 402 and measures the current amplitude $I_{0.04\,Hz}$ and $I_{1\,Hz}$ and measures the fluid temperature $T_F$.

The system then proceeds to compute the impedance for each of the measured currents $I_H$, $I_L$ at step 404.

The system then proceeds to step 406 and subtracts the value of $Z_H$ computed in step 404 from the value of $Z_L$ computed in step 404, to give the differential impedance $\Delta Z$.

The system then proceeds to step 408 and enters a lookup table containing stored values of $A_Z$ as a function of temperature $T_F$ at various known fluid conditions and finds the fluid condition based upon $\Delta Z$, $T_F$ from step 406 and $T_F$ from step 402. The system then proceeds to step 410 and makes a determination whether the fluid condition determined in step 408 is less than a predetermined critical threshold. If the determination in step 410 is affirmative, the system returns to step 400. However, if the determination in step 410 is negative, the system proceeds to activate an operator warning at step 412 and/or displays the fluid condition at step 414.

Figure 10:
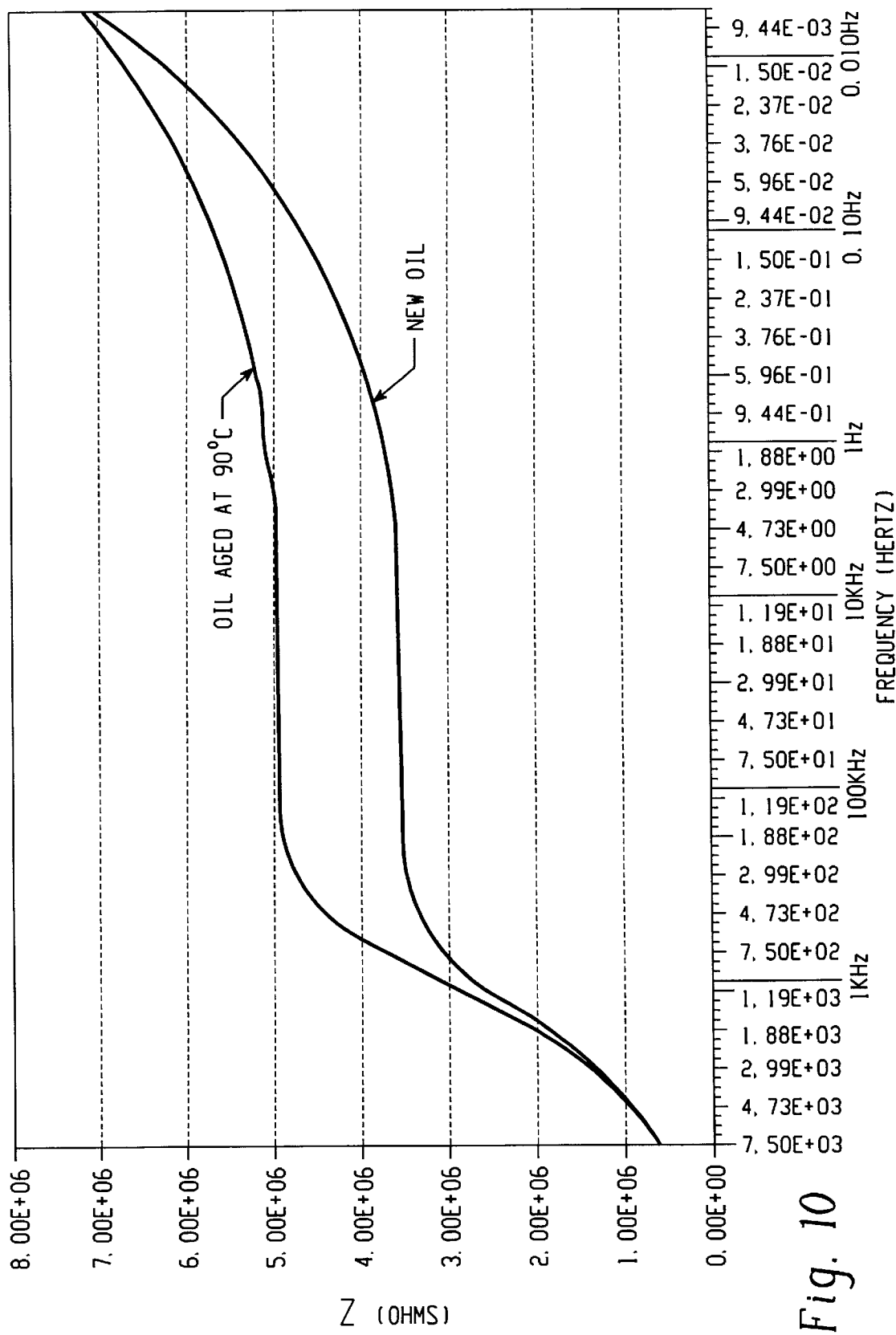
FIG. 10 is a graph of values of impedance plotted as a function of frequency for the spirally wound probe of FIG. 5 of the present invention in synthetic motor oil; and, FIG. 11 is a graph of percent (%) change from uncontaminated fluid as a function of excitation voltage frequency for ATF 1% engine coolant contamination measured with the invention spiral probe.

Referring to FIG. 10, measurements of impedance AZ ΔOhms) for 5W30 synthetic passenger car motor oil (PCMO) taken with the invention spiral probe of FIGS. 1–4 are plotted as a function of excitation current frequency for new and aged oil. From FIG. 10, it will be seen that the spiral probe produces significant and easily detectable change in impedance between the high and low frequencies and is thus a useful device for measuring the change in oil condition.

Figure 11:
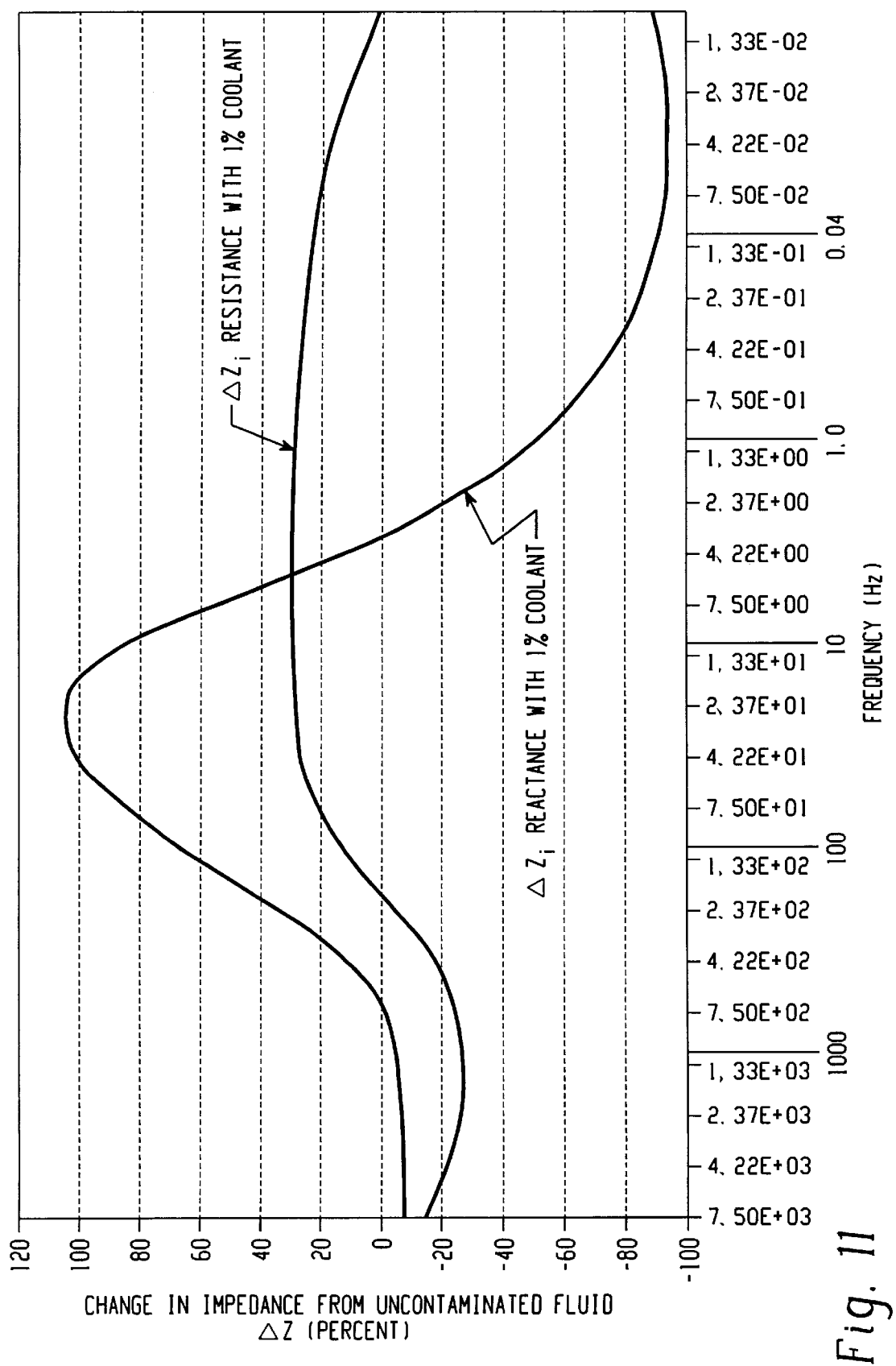

Referring to FIG. 11, values of the change in impedance $\Delta Z$ in percent (%) are plotted as a function of frequency of the excitation current for measurements taken with the invention spiral probe immersed in commercially available automatic transmission fluid contaminated with one percent (1%) engine coolant containing glycol based antifreeze. From FIG. 11 it will be seen that at the high and low frequencies employed in the present invention, nearly 100% change in reactive impedance Zi occurred between measurements of contaminated and uncontaminated fluid, thus demonstrating the usefulness of the spiral probe in detecting contamination in transmission fluid.

The present invention thus provides a unique and novel spirally configured probe for measuring in real time the condition of a fluid to be monitored by relatively low voltage, low current measurement by exciting the probe at a relatively low voltage and low current sequentially at a fractional Hertz (low) frequency and then at a (high) frequency current of at least one Hertz.

The current is measured at both the high and low frequencies and the impedances $Z_H$, $Z_L$ are computed. This difference in impedance $\Delta Z$ is then computed from $Z_H$, ZL. From a lookup table of stored valves of $\Delta Z$ as a function of temperature at various fluid conditions, the fluid condition for the computed $\Delta Z$ and measured temperature is then found. If the determined fluid condition is found to be less than a preset threshold or critical value, the system can activate an operator alarm and/or display the determined fluid condition.

Although the invention has hereinabove been described with respect to the illustrated embodiments, it will be understood that the invention is capable of modification and variation and is limited only by the following claims.

What is claimed is:

1. A sensor probe assembly for monitoring the condition of a fluid through an opening in a vessel comprising:
   (a) a base structure for mounting as a closure in said opening in the vessel and including means operable for effecting a seal about the opening;
   (b) a support structure extending from the base structure for immersion in the fluid vessel;
   (c) a pair of spaced generally parallel conductors disposed on said support structure and including at least one electrical lead extending through said base structure for effecting electrical connection to said conductors externally of said vessel;
   (d) a temperature sensor including circuitry for generating a fluid temperature $T_f$; and,
   (e) circuit means operable upon connection to a source of power to
      (i) excite one of said conductors sequentially with relatively high frequency voltage for measuring the effect of bulk fluid impedance and a relatively low frequency voltage for measuring the effect of surface electrode impedance;
      (ii) measure the current in said pair of electrodes at the high and low frequencies and compute the impedance difference from the measured currents;
      (iii) find the fluid condition from a look-up table of values of $\Delta Z$ as a function of $T_f$ for various known fluid conditions.

2. The probe assembly defined in claim 1, wherein said support structure has said pair of conductors helically wound thereon in generally uniformly spaced parallel arrangement.

3. The probe assembly defined in claim 1, wherein said circuit means includes circuitry for exciting the one electrode at a low frequency of less than one Hertz.

4. The probe assembly defined in claim 1, further comprising a thermistor disposed on said support structure and said at least one lead is connected through said base structure to said thermistor.

5. The probe assembly defined in claim 1, wherein said conductors are disposed in spirally interdigitated arrangement.

6. The probe assembly defined in claim 1, wherein said circuit means includes circuitry for exciting said one electrode at a high frequency of at least one Hertz.

7. The probe assembly defined in claim 1, wherein said base structure comprises a plug having a threaded portion with said support structure extending therefrom and an enlarged diameter flange portion.

8. The probe assembly defined in claim 7, wherein said lead means extends externally from said enlarged diameter flange portion.

9. The probe assembly defined in claim 1, wherein said support structure includes surfaces having a relatively low dielectric constant contacting said conductors.

10. A method of monitoring the condition of a fluid in a vessel comprising:
    (a) disposing a plug in an opening in said vessel and extending a support from the plug into the fluid in the vessel and sealing about said opening;
    (b) disposing a pair of spaced conductors in spiral arrangement on said support and connecting lead means therefrom through said plug for external connection;

(c) measuring the temperature of the fluid in the vessel and providing an electrical signal indicative thereof;

(d) exciting said conductors with a relatively low alternating voltage sequentially at a (high) frequency of at least one Hertz and at a second (low) frequency less than said first frequency;

(e) measuring the current at said first and second frequency excitation and computing a parameter therefrom;

(f) comparing said parameter and temperature with values of said parameter as a function of temperature for known fluid conditions and determining the condition of the fluid in the vessel.

11. The method defined in claim 10, wherein said step of disposing a pair of conductors includes helically winding said conductors on said support.

12. The method defined in claim 10, wherein said step of measuring temperature includes disposing a thermistor on plug and connecting electrical leads through said plug to said thermistor.

13. The method defined in claim 10, wherein said step of computing a parameter includes computing impedance difference at low and high frequencies.

14. The method defined in claim 10, wherein said step of disposing a pair of conductors includes helically winding said on said support.

15. The method defined in claim 10, wherein said step of extending a support from said plug includes forming said support of polytetrafluoroethylene material.

16. A method of monitoring the condition of a fluid in a vessel by low voltage low current measurement comprising:

(a) disposing a pair of spaced electrodes in spiral arrangement in the fluid;

(b) applying a substantially constant alternating voltage sequentially to said electrodes at a relatively low frequency for measuring the effect of surface electrode impedance and at a relatively high frequency for measuring the effect of bulk fluid impedance;

(c) measuring the current in said electrodes at said high and low frequencies and computing the difference in impedance $\Delta Z$ at said measured currents; and, (d) determining the condition of the fluid from a look-up table of values of $\Delta Z$ as a function of known fluid conditions.

17. The method defined in claim 16, wherein said step of disposing a pair of electrodes includes helically winding a pair of wires on a support in spaced parallel arrangement.

18. The method defined in claim 16, wherein said step of applying a voltage at a relatively low frequency includes applying a voltage at a frequency less than one Hertz.

19. The method defined in claim 16, wherein said step of applying a voltage at a relatively high frequency includes applying a voltage of at least one Hertz.

* * * * *